United States Patent
Sigsbee

(10) Patent No.: US 11,610,221 B2
(45) Date of Patent: Mar. 21, 2023

(54) INTEGRATED PRESCRIPTION OFFER PROGRAM AND APPARATUS

(71) Applicant: PDR, LLC, Whippany, NJ (US)

(72) Inventor: Will Sigsbee, Minneapolis, MN (US)

(73) Assignee: PDR, LLC, Whippany, NJ (US)

( * ) Notice: Subject to any disclaimer, the term of this patent is extended or adjusted under 35 U.S.C. 154(b) by 135 days.

(21) Appl. No.: 16/997,628

(22) Filed: Aug. 19, 2020

(65) Prior Publication Data

US 2021/0217044 A1    Jul. 15, 2021

Related U.S. Application Data

(60) Provisional application No. 62/903,472, filed on Sep. 20, 2019.

(51) Int. Cl.
*G06Q 30/02* (2012.01)
*G06Q 30/0234* (2023.01)
*G16H 10/60* (2018.01)

(52) U.S. Cl.
CPC ......... *G06Q 30/0234* (2013.01); *G16H 10/60* (2018.01)

(58) Field of Classification Search
CPC .... G06Q 30/0234; G16H 10/60; G16H 20/10; G16H 40/20
See application file for complete search history.

(56) References Cited

U.S. PATENT DOCUMENTS

| 2002/0049615 | A1* | 4/2002 | Huber | G16H 40/67 705/3 |
| 2008/0065490 | A1* | 3/2008 | Novick | G06Q 30/0225 705/14.39 |
| 2015/0058627 | A1* | 2/2015 | Paffel | G16H 10/60 713/168 |
| 2019/0252049 | A1* | 8/2019 | Fotsch | G16H 40/20 |

OTHER PUBLICATIONS

University of Chicago, Is there an App for That EHR and Conflict Prevention and Resolution, P Dullabh (Year: 2011).*

* cited by examiner

*Primary Examiner* — Breffni Baggot
(74) *Attorney, Agent, or Firm* — Lewis Rice LLC

(57) ABSTRACT

The present invention relates to a method and apparatus for providing discounts, rebates, and offers relating to various medicines or supplements as integrated into an electronic health record application. The invention uses one or more computer systems to send and receive signals from an electronic health record application. The information is used to consult various databases to find offers regarding health products prescribed or recommended to a person.

8 Claims, 3 Drawing Sheets

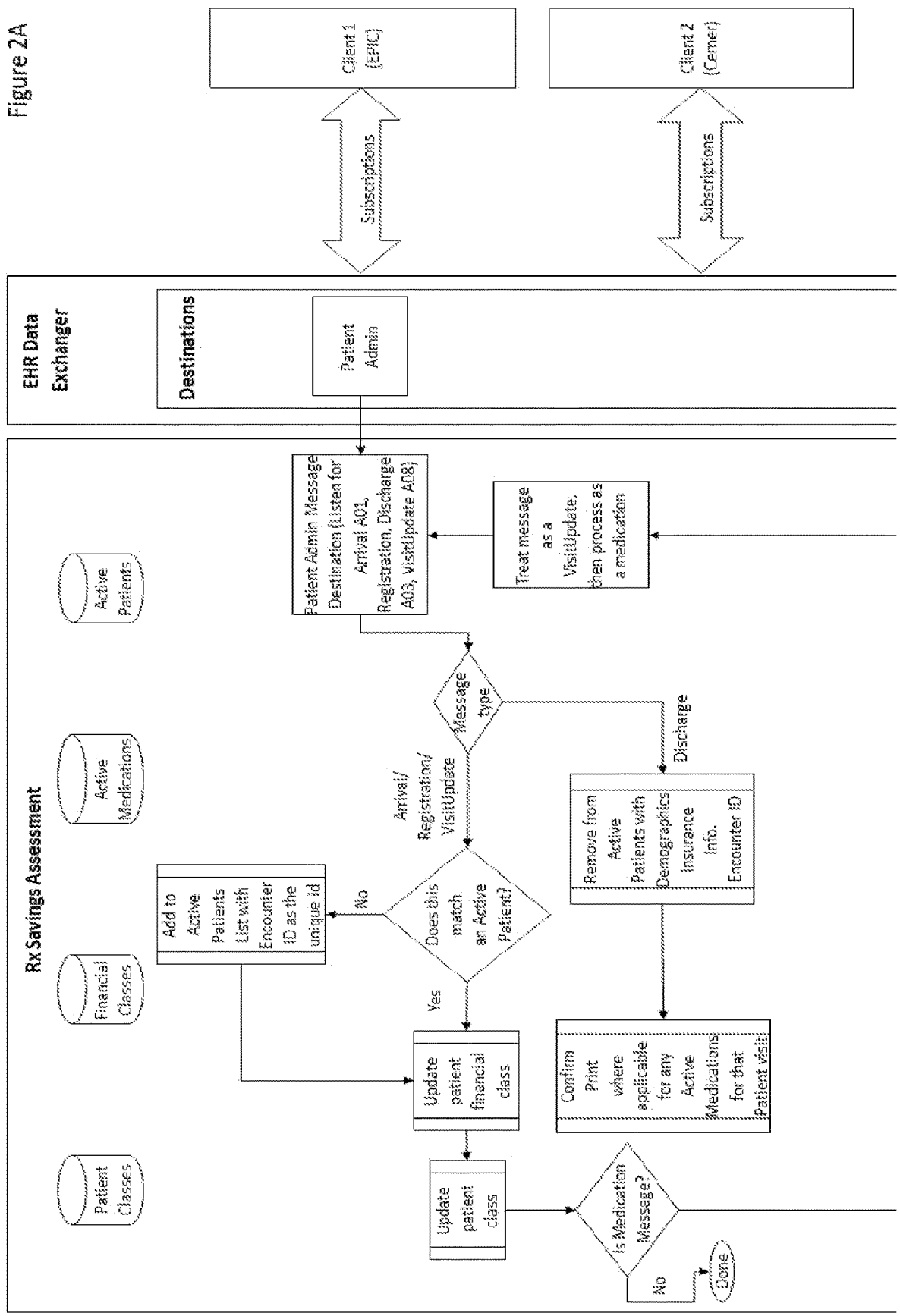

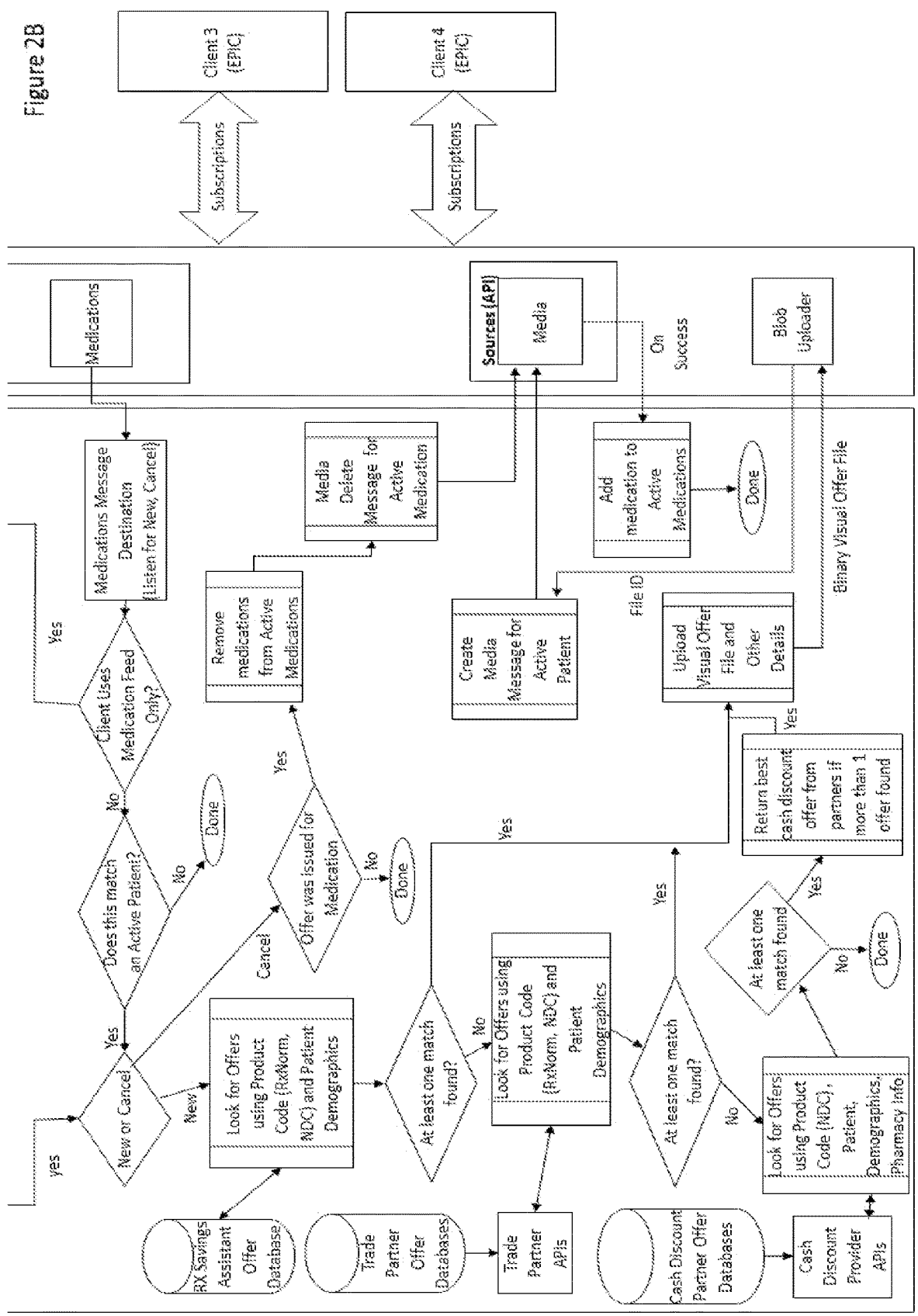

INTEGRATED PRESCRIPTION OFFER PROGRAM AND APPARATUS

RELATED APPLICATION

The present application claims priority to and incorporates by reference U.S. Provisional Patent Application No. 62/903,472 filed on Aug. 20, 2019.

BACKGROUND OF THE INVENTION

Field of the Invention

The present invention relates to a method and apparatus for providing discounts, rebates, and offers relating to various medicines or supplements as integrated into an electronic health record application.

Background

Electronic health records ("EHR") have become quite common in the fulfillment of professional health services, such as medical, dental, or veterinary fields. EHRs, however, suffer from a number of drawbacks. Data entry is often difficult and adds substantially to the amount of work that clinicians and support staffs need to perform. They are complex and difficult to use and interpret. Further, they come in a wide variety of forms shapes and sizes, which creates substantial issues relating to interoperability.

Also, the ability of the EHR to work with third party software and service applications has complicated the ability to provide complimentary services to users and patients. In particular, many patients visit a health care provider for treatment and receive medication assignments either for prescribed medication, or for over-the-counter products and the like. This information is tracked in the EHR system, however, heretofore there has been no effective way to integrate that medication order information with information from manufacturers of such products in an automated fashion to try and guide and assist the patient's purchasing decision.

The complexity of the EHR systems and the difficulty in interacting with outside applications have presented substantial obstacles that have not been overcome by the prior art. Thus, a need exists for a system that can extract information from an EHR to assist a patient in the purchase of medications, health and nutrition products, and the like associated with the patient's treatment.

BRIEF DESCRIPTION OF THE FIGURES

FIG. 2A and FIG. 2B are a more detailed block diagram of a portion of the components shown in FIG. 1.

DETAILED DESCRIPTION OF THE INVENTION

Figure 1:
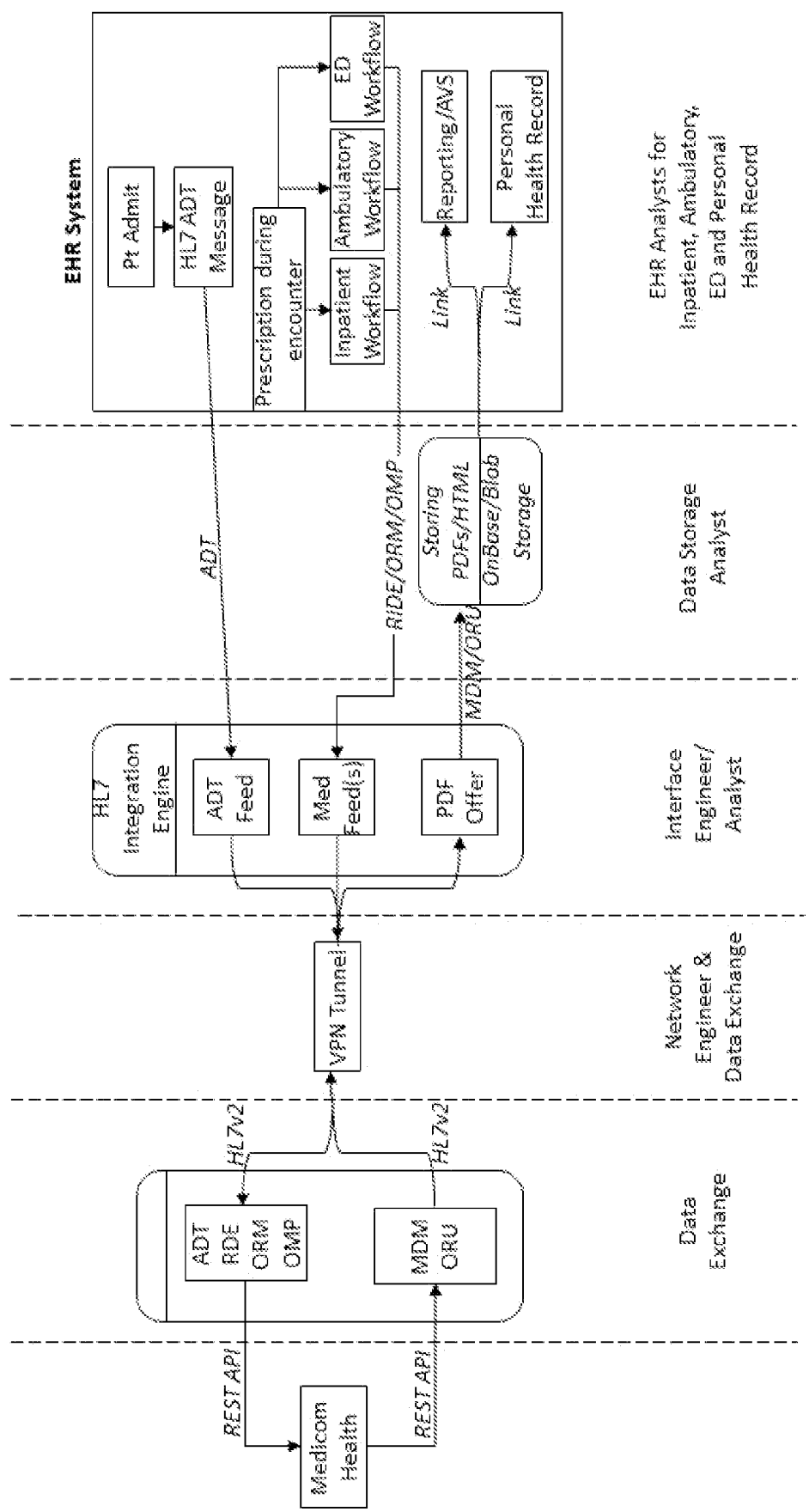
FIG. 1 is a block diagram of the components of the present invention.

The present invention at a high level, monitors the real-time information from an EHR system for a patient arrival or update events, the system also monitors prescription feeds coming from the EHR software for medications (or similar or other health related products) prescribed or assigned through the EHR, various databases are consulted to look for offers/discounts/rebates and the like applicable thereto, and if any are found the patient's EHR record is updated with the applicable information, and a file is generated with the offer information that is provided to the EHR which is automatically provided to the patient (either printed or electronically via email or by text) with discharge reports, visit summaries and the like, and given to the patient and automatically made available electronically in the EHR patient portal for repeat use.

FIG. 1 shows a high-level diagram of the system of the present invention. The invention monitors in real time certain information feeds from an EHR system, shown in the right most box in FIG. 1. As shown in FIG. 1, the process begins with an ADT event (often an admit event). The EHR includes an admit or ADT feed pursuant to the HL7 standard for the exchange of electronic health information. The ADT feed, which generally stands for Admit, Transfer, and Discharge, carries a great deal of patient information in addition to admit, transfer, and discharge status which is available to the system of the present invention. The EHR System generates messages on the ADT feed, which the present invention monitors and uses as a trigger for further action as described below.

The EHR System also tracks information regarding a patient's prescription activity including when a new prescription is assigned to the patient. The present invention works with the inpatient, ambulatory, and Emergency Department (ED) workflows to track patient prescription encounters as documented in the EHR Systems, however, the invention is not limited to these particular flows. These prescription related events/activities are documented in various HL7 feeds provided through the EHR, including the RDE (pharmacy/treatment encoded order message), ORM (general order message), and OMP (pharmacy/treatment order message) feeds, which are also monitored by the present invention.

Thus, the present invention monitors two main feeds from the EHR, the ADT feed in order to follow any active patients in the EHR System, and the RDE/ORM/OMP feeds in order to know when an active patient has been prescribed a medication, supplement, health product, or other similar products.

The relevant feeds are typically sent through a commercially available HL7 integration engine for the purpose of managing the deliver or, and standardizing the feeds. The HL7 message system uses a number of different formats, and EHR vendors and other application providers do not all use the same formats. In order to standardize communication across multiple systems an integration engine is used to avoid having to individually adapt the system to each different EHR vendor's protocols. Of course, the integration engine does not have to be used, but it does provide for efficient standardization. Thus, the integration system takes the incoming feeds described above, and outputs a standard feed. The HL7 integration engine provides additional feed transformation capabilities, debugging tools, and advanced IT management capabilities for the health system.

Up until this point the activity is typically taking place on systems under the healthcare provider's control. The VPN tunnel shown in FIG. 1 is the dividing line between the healthcare provider system to the right, and the outside system/systems to the left, wherein the VPN tunnel is a bridge between the two. A VPN tunnel is established between the healthcare provider system and the system upon which the bulk of the present invention operates on. The VPN tunnel provides a secure pathway for communication between the two systems, especially in view of the fact that sensitive patient health information is involved.

Next, the information from the EHR is normalized through the a commercially available data exchange service, which provides additional data integration and standardization services on the side of the system operating on the other side of the healthcare provider system. Due to the complexities of EHR and healthcare data processing systems, a data exchanger is helpful in reducing the level of customization needed to handle information coming from different EHR systems, or even different HL7 integrators. Of course, the present invention can be carried out without a data exchanger by customizing the system to each EHR/HL7 integration engine standards.

The data exchanger communicates using APIs with the proprietary system of the present invention, which performs the function of monitoring active patients identified through the ADT feed, while also listening for any medication assignments on the various medication feeds.

In the event that an active patient is prescribed a medication, then the system consults a variety of databases that store information about the medication including information about any discounts, rebates, offers, and the like. If a match is found, the system dynamically generates a file that visually represents the offer, which is intended to be printed and given to the patient detailing the offer and provided electronically through the EHR system. The patient can then take that with them to use when they go to the pharmacy or other establishment where they purchase or obtain the subject medication.

The dynamically generated file is sent back to the data exchanger through an API call. The data exchanger returns the information to the health system via an MDM (medical document management) feed or an ORU (observation results) feed. These MDM or ORU feeds are available in general to help place information in a patient's record within the EHR, by transmitting documents for placement therein. Alternatively, the document can be delivered to a Secure FTP (SFTP) server, or distributed through a link via a HL7 feed where the document is stored on a remote server. In any event, the purpose is to send back to the EHR a document that can be saved to a patient record and printed for the patient at the point of care to take with them. The MDM/ORU message is then transferred through the VPN tunnel to the healthcare provider system, through the HL7 integration engine, and then to the EHR storage system for use in the health record. The file is then stored in the health record either in an EHR document server, or in a blob storage area typically used to store unstructured data of various types accessible from the EHR system.

The file is stored according to a unique encounter or visit identification value generated by the EHR system, and its document type descriptor (such as RxSA Voucher), for later retrieval and so that it can be pulled into the patient's discharge report, and printed for the patient to take with them. An electronic copy is also linked to the patients' EHR record and can be obtained and printed later by the patient. For example, the record can be made available to the patient through their own personally accessible part of the health record (called MyChart in some systems), where it will remain for some predefined period of time.

The system of the present invention is shown in greater detail in FIGS. 2A and 2B. In particular, FIGS. 2A and 2B are a detailed view of the portion of the system identified in FIG. 1 as Medicom Health. The process begins in the upper right-hand corner, with the portion of the system that receives the ADT feed. In particular, the system is listening to the ADT feed for arrivals (patient arrives at a health care provider facility and is checked into the EHR), registration (similarly, a patient is registered in the EHR), discharge (patient is no longer available for treatment or active in the system which can happen for various reasons—for example, the patient treatment is complete, or the patient left after checking in but before treatment, or the patient dies), and patient update (may indicate the return or updating of an existing patient that is again available for treatment).

The system then processes each of the four types of events from the ADT feed as set forth. For events where we receive an arrival, registration, or a patient update event, the system consults the database to determine if the patient is already an active patient, and if not, the patient is added to the system's active patient list, and a unique encounter ID is created for the patient. If the patient is active then the patient's insurance information, which is carried by the ADT feed, is updated in case any changes have been made.

The arrival/registration and patient update events are both used by the system to update the patient's financial class, which is provided by the EHR. A determination is made as to whether the financial class exists in the current tables, and if not, it is added to the tables. The financial class typically determines if the patient has private insurance, if self-pay (no insurance), or has a government payer. If the patient has a financial class or insurance that is classified as private or self-pay, the patient is eligible for offers. For example, patients with government payers are only eligible for free trial offers from select manufacturers currently, however, the invention is not necessarily limited thereby.

If the ADT event is a discharge, meaning the patient is no longer available for treatment, then the patient is removed from the active list meaning the system no longer needs to monitor the medication feeds for this patient, and a print step is confirmed where applicable for any active medications associated with the patients visit.

Next, the processing of the medication feeds is detailed. The system is monitoring the aforementioned medication feeds for active patients listening for any new medications being assigned to the patient, or for the cancelation of any existing active medications. The new or cancel signal is parsed. If the medication was cancelled, then if an offer had recently been issued the medication is removed from the active medications list for the patient, and a media delete message is sent over the MDM feed (if available) to the EHR to delete any prior offers from the patient's record. If no coupon had been issued then nothing needs to be done.

If the medication is new, the system determines if the patient still has an active status, and if so whether the patient has approved insurance (that determination described above). If the patient is active and insurance information is available, then the system consults a proprietary internal database of offers to look for direct offers using the available product code and patient demographic information. For example, the system can perform this look up using the RxNorm normalized names of clinical drugs, which is provided through the U.S. National Library of Medicine, or using the NDC (National Drug Code) which is a unique product identifier code used in the United States. If an offer is found, then a visual offer file (typically in PDF or image file format) is generated and uploaded to the EHR via the MDM or ORU feed. The system also can monitor the National Council for Prescription Drug Programs (NCPDP) code for the patient's pharmacy of choice (if available) which can be used to personalize the offers by providing pharmacy specific information tailored to an offer at a patient's pharmacy of choice. Other databases can be added as the foregoing are exemplary and the invention is not necessarily limited thereto.

If no match is found additional databases are consulted. The system consults multiple commercially available databases provided by Medicom's trade partners via API calls. If an offer is found, then a visual offer file is generated and uploaded to the EHR on the MDM or ORU feed.

If no match is found the system may optionally consult a database of cash discount offers. The system consults a commercially available database provided by cash discount offer trade partners via API calls. If an offer is found, then a visual offer file is generated and uploaded to the EHR on the MDM or ORU feed.

If no match is found in any of the databases, then no action is taken. If a match has been found, as described above a visual offer file is generated, a unique file ID is created, and that information is sent to the EHR.

Information about the foregoing can be printed and provided to a patient that had a medication assigned, a positive response from the databases yielding a discount offer for the prescribed medication. The information includes the actual offer. Also, as described, a record of this information is provided to the EHR and made available in a patient accessible portion of the EHR, which they can view or print at a later date. The offer information optionally can be removed from the EHR in the event that the offer has expired, or after some predetermined period of time as appropriate.

Operation of the present invention requires consideration of several factors, especially with regard to the healthcare providers EHR implementation. In particular, consideration needs to be taken of whether the healthcare provider uses the same EHR system across the entire system of if multiple EHRs are used; the workflow for how medications are routed throughout the system needs to be understood in particular if there are variations for ambulatory, ED, and inpatient processing; the HL7 feeds for the EHR need to be examined to determine what types of messages are supported and what information is coming out of the system for ambulatory, ED, and inpatient disciplines; determine if the EHR supports MDM or ORU messages coming back into the EHR; and determine what data exchange and HL7 integration systems are supported by the EHR. These and other considerations will need to be understood during and after implementation.

The following is list of more detailed specification for the present invention; however, the invention is not necessarily limited thereto. The system utilizes the following HL7 feed requirements: RDE/OMP/ORM v2 feed (for medication prescription events within the clinical workflow); MDM/ORU v2 feed (for returning offer media for distribution); and ADT HL7 v2 feed (for clinical events and patient demographic info).

The present invention utilizes the following data requirements.

Data needed for configuration:
  Document Type—This should be a unique document type that will be used to create and find the offers that have been delivered to the EHR for the patient and attached to the patient's printed summary report
  Provider ID—This can be a generic Provider ID assigned to the relevant treating health care professional for external data sources and is needed when the offer is sent back to the EHR through the returning HL7 media feed (MDM/ORU)
  Provider first name—This can be generic and may be required by a system when the offer is sent back to the EHR through the returning HL7 media feed (MDM/ORU)
  Provider last name—This can be generic and may be required by a system when the offer is sent back to the EHR through the returning HL7 media feed (MDM/ORU)

Data that can be included in feeds/messages:
  ADT A01/A04/A08 Message (PID):
    Patient Identifier—can be generated on client side and does not have to be MRN
    Date of Birth— age is required, can accept age in lieu of date of birth
    Patient State
    Patient Zip Code—optional field, required for cash pay offers
    Patient Sex
  ADT A01/A04/A08 Message (PVI):
    Visit Number
    Patient Class—Outpatient, Inpatient, etc.
    Financial Class—Medicare, Commercial, Medicaid, etc.
  Medication Data (RDE/OMP/ORM):
    Medication Code
    Medication Name (preferred)
    Medication Quantity
    Medication Dispense Frequency
    Pharmacy NPI
    Pharmacy Code— NCPDP
    Pharmacy Address (preferred)
    Patient Zip Code—optional field, required for cash pay offers The data outlined above can be sent to from the EHR using the following feed types.
  Medication Feed(s)—During the time the patient is in an encounter, the system listens for medication orders, for which it attempts to match offers. These medications orders can be sent through the following message types:
  ORM_001 HL7 v2
  RDE_011 HL7 v2
  OMP_009 HL7 v2
  The standard segment information is shown below for these message types, but some health systems may choose to use different segments based on their configurations.

| Segment | SEQ | Name | Data Type | Required/Preferred |
|---|---|---|---|---|
| PID | PID.2 | Patient ID | CX | Required |
| PID | PID.7 | Date/Time of Birth | TS | Required |
| PID | PID.8 | Administrative Sex | IS | Preferred |
| PID | PID.11.4 | State or Province | ST | Required |
| PID | PID.11.5 | Zip or Postal Code | ST | 3-digit zip code preferred/5-digit zip code required for geo-located cash pay offers only |
| PV1 | PV1.2 | Patient Class | IS | Preferred |
| PV1 | PV1.3 | Assigned Patient Location | PL | Preferred |
| PV1 | PV1.3 | Patient Location Type | IS | Preferred |
| PV1 | PV1.19 | Visit Number | CX | Required |
| PV1 | PV1.20 | Financial Class | FC | Preferred |
| ORC | ORC.1 | Order Control | ID | Required |
| ORC | ORC.2 | Placer Order Number | EI | Required |
| ORC | ORC.7 | Quantity/Timing | TQ | Required |
| ORC | ORC.12 | Ordering Provider | XCN | Preferred |
| ORC | ORC.22 | Ordering Facility Address | XAD | Preferred |
| RXO | RXO.1 | Requested Give Code | CWE | Required |

-continued

| Segment | SEQ | Name | Data Type | Required/Preferred |
|---|---|---|---|---|
| RXO | RXO.11 | Requested Dispense Amount | NM | Required |
| RXO | RXO.12 | Requested Dispense Units | CE | Required |
| RXO | RXO.32 | Dispensing Pharmacy | CWE | Preferred |
| RXO | RXO.33 | Dispensing Pharmacy Address | XAD | Preferred |

The following is a list of expected ADT messages:

| Segment ID | Description | Required/Preferred |
|---|---|---|
| A01 | Admit/visit notification | Either A01, A04 or A08 is Required |
| A04 | Register a patient | Either A01, A04 or A08 is Required |
| A08 | Update patient information | Either A01, A04 or A08 is Required |
| A03 | Discharge/end visit | Preferred for Ambulatory/Required for ED and Inpatient |

A01/A04/A08 segment requirements:

| Segment | SEQ | Name | Data Type | Required/Preferred |
|---|---|---|---|---|
| PID | PID.1 | Patient ID | CX | Required |
| PID | PID.7 | Date/Time of Birth | TS | Required unless age provided in Z segment |
| PID | PID.8 | Administrative Sex | IS | Required |
| PID | PID.11.4 | State or Province | ST | Required |
| PID | PID.11.5 | Zip or Postal Code | ST | 3-digit zip code preferred/5-digit zip code required for geo-located cash pay offers only |
| PV1 | PV1.2 | Patient Class | IS | Required |
| PV1 | PV1.3 | Assigned Patient Location | PL | Preferred |
| PV1 | PV1.19 | Visit Number (CSN) | CX | Required |
| PV1 | PV1.20 | Financial Class | FC | Required |
| Z | | Age | | Can accept in lieu of date of birth |

Segment requirements are the same for A03 messages if they can be provided.

If the system is able to find an offer for a medication that was sent over from the EHR, the system will send back the visual offer file in PNG, JPG, TIFF, PDF or HTML format through one of the following message types:

MDM_T02 HL7 v2 (preferred)
ORU HL7 v2

The system will also return whatever additional ID requirements that the EHR/health system needs for reattaching the offer back to the patient encounter.

The offer will need to be sent to a document storage location, often either blob storage located in the EHR system or a third-party system.

If the MDM message type is chosen, the system can also send back a scheduled T11 message after a specific number of days from when the original T02 message was sent. This can help with document retention and the amount of storage needed.

The offer can be displayed in the following ways: at the end of the patient's discharge/after visit paperwork (required if paperwork is provided); and/or included in the patient's Personal Health Record section of the EHR.

If coded values are sent in the HL7 messages, a table needs to be provided to translate the values. The values below are common for the data models used, but only the applicable ones need to be provided.

| Concept | Field |
|---|---|
| Patient | Sex |
| Patient | Patient Class |
| Insurances | CoverageType |
| Insured | Relationship |
| Orders | Priority |
| Media | Availability |
| Media | Authenticated |

The above specification and accompanying Figures are for illustrative use only. The scope of the present invention will be defined by the claims. The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention. Those of ordinary skill in the art that have the disclosure before them will be able to make modifications and variations therein without departing from the scope of the invention. In particular, the present invention can be carried out by monitoring the medication feeds, without necessarily relying in addition on the ADT feed. The invention can be carried out without the assistance of an HL7 integration engine, or a data exchange service by integrating and adopting the system to each EHR's requirements and protocols.

The invention claimed is:
1. A method for integrating electronic health record (EHR) systems with external applications for real-time synchronizing of supplementary product information in EHR records, said method comprising:
providing a healthcare provider computer server of a healthcare provider, said healthcare provider computer server having an EHR system operating thereon, said EHR system having a plurality of personal health records, each of said personal health records in said plurality of personal health records associated with a specific patient of said healthcare provider;
providing a supplementary product information computer server of a third party to said healthcare provider and communicably coupled to said healthcare provider computer server via a telecommunications network, said supplementary product information computer server having a list of active patients receiving medical treatment, and being communicably coupled to a plurality of databases having supplementary product information about a plurality of products;
transmitting, by said healthcare provider computer server via said telecommunications network, a first data feed comprising data about medical treatment encounters between said healthcare provider and said patient of said healthcare provider, including data regarding the healthcare status of said patient;
transmitting, by said healthcare provider computer server via said telecommunications network, a second data feed comprising data about the product status for said patient;
in association with said healthcare provider providing medical treatment to said patient:

generating, by said EHR system, a unique encounter identifier associated with said medical treatment of said patient;

associating, by said EHR system, said generated unique encounter identifier with a first personal health record of said plurality of personal health records, said first personal health record being associated with said patient;

transmitting, by said EHR system via said first data feed, a patient identifier associated with said patient, an indication of a patient eligibility status, and an indication of a treatment status of said patient during said medical treatment;

transmitting, by said EHR system via said second data feed, said patient identifier and product identifier associated with a product prescribed to said patient during said medical treatment;

in response to receiving, at said supplementary product information computer server via said first data feed, said transmitted patient identifier, said indication of a patient eligibility status, and said indication of a treatment status, said supplementary product information computer server synchronizing said list of active patients based upon said received patient identifier, said indication of a patient eligibility status, and said indication of a treatment status, said synchronizing comprising:

comparing said list of active patients to said transmitted patient identifier and said indication of a treatment status;

adding said patient to said list of active patients where said patient is not on said list of active patients and said treatment status illustrates that said patient is active;

updating said list of active patients to include said indication of a treatment status of said patient where said patient is active;

monitoring said first data feed for additional transmitted data about said patient identifier;

in response to receiving, at said supplementary product information computer server via said second data feed, said transmitted patient identifier and said transmitted product identifier;

said supplementary product information computer server:

determining whether said patient is eligible for said supplemental product information for said product associated with said transmitted product identifier; said determination comprising:

confirming said patient is listed within said list of active patients;

confirming said product associated with said transmitted product identifier is listed within one or more of said plurality of databases having supplementary product information about a plurality of products; and confirming that said patient is eligible to receive supplementary product information for said product associated with said received product identifier by comparing against information stored in said one or more of said plurality of databases having supplementary product information about a plurality of products;

if, based on said determining, said patient is eligible for said supplementary product information for said product associated with said received product identifier:

generating a visual file comprising supplementary product information for a product associated with said product identifier;

transmitting, to said EHR system via said telecommunications network, a copy of said visual file and said patient identifier;

receiving, at said healthcare provider computer server, said copy of said visual file and said transmitted patient identifier;

after said medical treatment of said a patient;

providing said copy of said visual file in association with a discharge report generated in association with said medical treatment of said patient; and said patient receiving a copy of said generated discharge report and said received visual file.

2. The invention of claim 1 where the visual file can be visually viewed by the patient.

3. The invention of claim 2 where the visual file is rendered as a document attached to the patient's personal health record in the EHR system.

4. The invention of claim 2 where the visual file is rendered as a document that is printed for the patient.

5. The invention of claim 1 where the visual file is a rebate, discount, or other monetary incentive associated with the product.

6. The invention of claim 1 wherein if, supplementary product information is listed in more than one of said plurality of databases and, based on said determining, said patient is ineligible for said supplementary product information from a first of said plurality of databases, said supplementary product information computer server determines if said patient is eligible for said supplementary product information from another of said plurality of databases.

7. The invention of claim 1 where each visual file is given a unique identification number for later reference.

8. The invention of claim 1 where the product is a medication.

* * * * *